Figure 1:
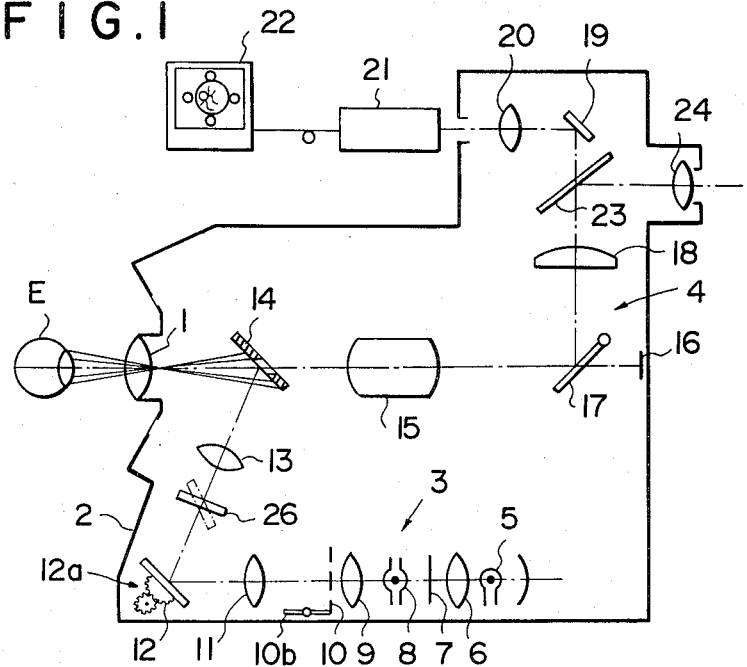

United States Patent [19]

Sano et al.

[11] 4,405,215
[45] Sep. 20, 1983

[54] WORKING POSITION LOCATING MEANS FOR OPHTHALMOLOGIC APPARATUS

[75] Inventors: Eiichi Sano; Kazuo Nunokawa, both of Tokyo, Japan

[73] Assignee: Tokyo Kogaku Kikai Kabushiki Kaisha, Tokyo, Japan

[21] Appl. No.: 318,001

[22] Filed: Nov. 4, 1981

[30] Foreign Application Priority Data

Nov. 14, 1980 [JP] Japan .................. 55-160161

[51] Int. Cl.³ .................. G03B 29/00; A61B 3/14
[52] U.S. Cl. .................. 351/208; 354/62
[58] Field of Search .............. 351/206, 208, 214, 207; 354/62

[56] References Cited

U.S. PATENT DOCUMENTS 4,196,979 4/1980 Kohayakawa et al. .

Primary Examiner—John K. Corbin
Assistant Examiner—Rodney B. Bovernick
Attorney, Agent, or Firm—Brumbaugh, Graves, Donohue & Raymond

[57] ABSTRACT

A working position locating device for an ophthalmologic apparatus in which the projected image of a ring slit aperture is offset from the projecting optical axis when the position of the apparatus is being changed so that the ring slit image be seen on the focal plane of the observation optical system, whereby the proper working position of the objective lens relative to the eye can be grasped from the position of the ring slit image.

6 Claims, 4 Drawing Figures

WORKING POSITION LOCATING MEANS FOR OPHTHALMOLOGIC APPARATUS

The present invention relates to a working position locating device for an ophthalmologic apparatus.

An ophthalmologic apparatus such as an eye fundus camera is constructed so that an illuminating beam of light is projected through an objective lens arranged to be opposed to an eye to be examined. In case where the apparatus is an eye fundus camera, the beam reflected at the fundus is passed through the objective lens into a photographic optical system. In not only the fundus camera but also an ophthalmologic apparatus of that kind, in which an illuminating beam of light is projected through an objective lens upon an eye to be examined and in which the reflected flux of light from the inside of the eye is guided into a photographic or observation optical system, there is a fear that the illuminating beam of light reflected at the cornea of the eye also enters the photographic or observation optical system and makes a flare or ghost.

In order to solve the problem of the flare or ghost due to the illuminating beam of light reflected at the cornea, according to the prior art, there has been adopted an arrangement in which a ring-shaped slit aperture is disposed in the illuminating optical system and an apertured mirror is obliquely arranged along the optical axis of the objective lens at a position substantially conjugate with the iris of the eye to be examined with respect to said objective lens so that the ring-shaped illuminating luminous flux of light having passed through the ring-shaped slit aperture be once focused upon the annular reflecting surface of the mirror and directed from the objective lens through the iris into the eyeball. In this arrangement, where the apertured mirror is placed substantially conjugate with the iris of the eye with respect to the objective lens, in other words, since the distance between the objective lens and the apertured mirror is invariable, where the distance between the objective lens and the iris of the eye, that is the working distance, is proper and the optical axis of the objective lens is aligned with the optical axis of the eye to be examined, it is possible to eliminate the flare or ghost resulting from the reflection of the illuminating beam of light by the cornea.

In the ophthalmologic apparatus of this kind, therefore, it is very important to maintain a proper working position with respect to an eye to be examined when the apparatus is used. The proper working position has been located in the prior art by the operator finely moving the apparatus while visually inspecting the image formed in the observation optical system, e.g., the image on a monitor TV when the illuminating light is infrared, or the image to be observed through an eyepiece lens when the illuminating light is visible. According to this method of the prior art, however, small amounts of flare or ghost are liable to be overlooked because both adjustment of the working distance and complicated operations such as the alignment adjustment of the optical axis of the objective lens with the optical axis of the eye and focusing are simultaneously required. Moreover, in the ophthalmologic apparatus in which the alignment adjustment and the focusing operation are performed using an infrared ray, it is very difficult to detect the light which has been scattered in the corneal or the crystalline lens, in the view of the image upon a TV set.

As means for solving the problem described above, there has been proposed a working position locating device which is disclosed in Japanese patent application No. 54-81631. The device thus proposed has a light receiving portion formed around the objective lens so that both the working distance between the objective lens and the corneal surface of the eye and the state of alignment may be detected from the position of the illuminating luminous light flux reflected by the cornea at the light receiving portion. The light receiving portion can be constructed of, for example, a light receiving plate arranged around and coaxial with the objective lens. In this case, it is judged that the working distance is proper when the radius of the inner circle of the image of the corneal-reflected luminous light flux on the surface of the light receiving plate is a prescribed size. Moreover, the state of alignment between the eye to be examined and the objective lens can be determined by whether or not the inner circle of the image on the light receiving plate is coaxial with the optical axis of the objective lens.

The working position locating device thus far described is far more advantageous in determining the working distance and the state of alignment than the device according to the prior art and can easily perform the necessary display at the focusing unit of the observation optical system if it uses an optical fiber or a photoelectric element in place of the light receiving plate. Nevertheless, the device under consideration focuses the ring slit image, reflected by the cornea of the eye to be examined, in the vicinity of the objective lens and not through the objective lens, so it still has the problem that it is liable to be influenced by external light.

It is, therefore, an object of the present invention to provide a device which can locate the proper working position more simply and reliably than the device according to the prior art using a ring slit image formed by the reflection upon the cornea of an eye to be examined.

Specifically, in the working position locating device according to the present invention when the position of the apparatus is being adjusted the projected image of a ring slit aperture is offset from the projection optical axis so that the ring slit image be seen on the focal plane of an observation optical system, whereby the proper working position of the objective lens relative to the eye can be grasped from the position of said ring slit image.

Figure 2:
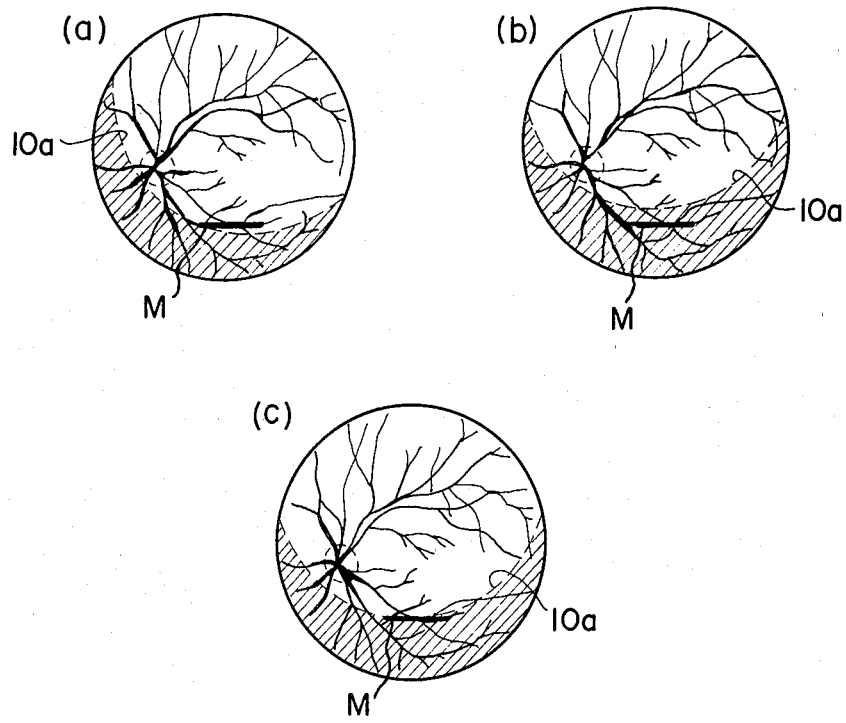

The above and other objects and features of the present invention will become apparent from the following descriptions of a preferred embodiment taking reference to the accompanying drawings, in which;

FIG. 1 is a schematic sectional view of an eye fundus camera showing one embodiment of the present invention; and, FIGS. 2(*a*), (*b*) and (*c*) are views showing the ring slit images on the focal plane of an observation optical system.

Referring now to the drawings, particularly to FIG. 1, there is shown an eye fundus camera which includes an objective lens 1 adapted to be placed opposite to an eye E to be examined, and a housing 2 containing an illumination optical system 3 and an observing-photographing optical system 4. The illumination optical system 3 is equipped with an illumination light source 5 for observation, and a light source 8 for photographing such as a xenon lamp which is arranged to face said light source 5 through a condenser lens 6 and a red filter 7. The light from each of the light sources is condensed by a condenser lens 9 to pass through a ring-shaped slit aperture 10 and a relay lens 11. The light is then reflected by a mirror 12 and passed through a relay lens 13 so that they are focused into a ring shape upon the reflecting surface of an apertured mirror 14 obliquely disposed on the optical axis of the objective lens 1. Then, the light is reflected by the reflecting surface of the mirror 14 to be projected through the objective lens 1 upon the eye E. The ring-shaped slit aperture 10 is located so that where the working distance is appropriate the image of the aperture 10 is produced at the anterior portion of the eye E, more specifically at the center between the front end of the cornea and the center of the curvature of the cornea.

The light reflected by the fundus of the eye E returns through the objective lens 1 into the fundus camera and through the center aperture of the mirror 14 into the observing-photographing optical system 4. This optical system 4 includes a focusing lens 15 so that the beam having passed through the focusing lens 15 is focused upon a film surface 15. In front of this film surface 16, a mirror 17 which can be popped up for photography is obliquely arranged so that its reflected beam is focused upon the focal plane of a field lens 18. The beam having passed through this field lens 18 is reflected by a mirror 19 and is focused upon the photoelectric surface of an image pickup tube 21 by a focusing lens 20. The signals from the image pickup tube 21 are fed to a monitor TV set 22 and an image is formed on its CRT. Another mirror 23 is obliquely arranged between the field lens 18 and the mirror 19 so that the beam reflected by that mirror 23 can be observed through an eyepiece lens 24. The mirror 23 may be constructed so that it can be removed as desired from the observation optical path.

In the illumination optical system 3, a parallel plane glass 26 is arranged at a suitable position, e.g., between the mirror 12 and the lens 13 and can be tilted from a position perpendicular to the optical axis of the illumination optical system 3 to an oblique position as indicated by phantom lines. The ring slit 10 is arranged coaxial with the projection optical axis so that it is projected coaxially with the optical axis of the illumination optical system, when the glass 26 is at its perpendicular position, as indicated by solid lines in FIG. 1, whereas its projected image is deviated or offset to an extent corresponding to the tilting angle when the glass 26 is tilted. The means for deviating the projected image of the ring slit may not necessarily be a parallel plane glass as illustrated but similar effects can be attained by changing the angle of the mirror 12 for example by a gear mechanism. Alternatively, the ring slit 10 may also be perpendicularly displaced with respect to the optical axis for example by a lever 10b. At this time, the ring slit 10 may be divided into slit components so that they can be displaced toward the optical axis, respectively.

In the example shown, in order to adjust the objective lens 1 of the fundus camera to the proper working position relative to the eye E to be examined, the parallel plane glass 26 is tilted to a predetermined extent, as shown by the phantom lines in FIG. 1, deviating the projected image of the ring slit aperture 10 to a predetermined extent in a predetermined direction. As a result, a ring slit image 10a as produced by the light reflected at the cornea appears to overlap the image of the fundus, as shown in FIGS. 2(a), (b) and (c). These images are observed by means of the eyepiece lens 24 or the monitor TV set 22. For example, if the horizontal alignment is not good, the ring slit image 10a is deviated laterally, as shown in FIG. 2(a); and if the vertical alignment is not good, the ring slit image 10a is deviated perpendicularly, as shown in FIG. 2(b). In the case of the proper alignment, the image 10a appears as shown in FIG. 2(c). The judgement can be conveniently performed if an index M is formed at the focal plane of the field lens 18 for indicating the edge position of the ring slit aperture at the proper state of alignment. Incidentally, the adjustment of the working distance is performed by adjusting the focused state of the edge of the ring slit image. Where the working distance is appropriate, the image 10a of the aperture 10 is produced on the focal plane. In taking photographs, the glass 26 may be returned to its perpendicular position indicated by the solid lines.

As has been described above, according to the present invention, since the ring slit image at the illumination optical system, i.e., the ring slit projection system is projected with a deviation relative to the optical axis so that the positions of the objective lens and the eye to be examined are judged from the position of the ring slit image at the focal plane of the observation optical system, the judgement can be performed easily and reliably, and the operations for locating the proper working position are made simple and convenient.

The invention has thus been shown and described with reference to a specific embodiment, however, it should be noted that the invention is in no way limited to the details of the illustrated arrangements but changes and modifications may be made without departing from the scope of the appended claims.

We claim:

1. An ophthalmologic apparatus including objective lens means adapted to be placed opposite to an eye to be examined, a ring-shaped slit projection system having an optical axis of projection and comprising ring slit aperture means substantially conjugate with an anterior portion of the eye with respect to the objective lens means and light source means for projecting an illuminating luminous flux through said slit aperture means and said objective lens means upon said eye to produce an image of said ring slit aperture means, an observation optical system for observing light which has passed from said eye through said objective lens means, said observation optical system having a focal plane, a working position locating means including means disposed in said ring-shaped slit projection system for deviating the image of said ring slit aperture means to a predetermined extent with respect to the optical axis of projection so that a proper working position with respect to said eye will be indicated by the position of the ring slit image upon the focal plane of said observation optical system.

2. An opthalmologic apparatus according to claim 1, wherein said deviating means includes optical means disposed in the optical path of said ring slit projection system for optically deviating projection of the ring slit aperture means.

3. An ophthalmologic apparatus according to claim 2, wherein said optical means is a parallel plane transparent element disposed for movement between a normal position wherein it is perpendicular to the optical axis of projection and a slanted position wherein it is inclined with respect to the optical axis.

4. An ophthalmologic apparatus according to claim 1, wherein said deviating means includes a mechanism for deviating said ring slit aperture means in a direction perpendicular to the optical axis of projection.

5. An ophthalmologic apparatus according to claim 1, wherein said slit projection system includes reflecting means for reflecting the luminous flux, said deviating means being means for changing a tilting angle of said reflecting means.

6. An ophthalmologic apparatus according to claim 1, wherein the focal plane of said observation optical system is formed with scale means for indexing a position of said ring slit image at an appropriate working position.

* * * * *